United States Patent [19]

Raiken

[11] Patent Number: 5,073,169
[45] Date of Patent: Dec. 17, 1991

[54] TROCAR SUPPORT

[76] Inventor: Steve Raiken, 5152 Pickford Way, Culver City, Calif. 90230

[21] Appl. No.: 624,294

[22] Filed: Dec. 7, 1990

Related U.S. Application Data

[63] Continuation-in-part of Ser. No. 591,969, Oct. 2, 1990, abandoned.

[51] Int. Cl.[5] ............................................. A61M 5/32
[52] U.S. Cl. .................................... 604/180; 604/174
[58] Field of Search ............... 604/174, 177, 180, 332, 604/344

[56] References Cited

U.S. PATENT DOCUMENTS

| | | |
|---|---|---|
| 2,898,917 | 8/1959 | Wallace . |
| 3,123,074 | 3/1964 | Turner . |
| 3,487,837 | 1/1970 | Petersen . |
| 3,893,446 | 7/1975 | Miller . |
| 4,464,178 | 8/1984 | Dalton . |
| 4,519,793 | 5/1985 | Galindo . |
| 4,579,120 | 4/1986 | MacGregor . |
| 4,593,681 | 6/1986 | Soni .............................. 604/174 X |
| 4,632,671 | 12/1986 | Dalton . |
| 4,675,006 | 6/1987 | Hrushesky . |
| 4,915,694 | 4/1990 | Yamamoto et al. . |

*Primary Examiner*—David J. Isabella
*Assistant Examiner*—Elizabeth M. Burke
*Attorney, Agent, or Firm*—Christie, Parker & Hale

[57] ABSTRACT

A trocar support comprising an elastomeric membrane having an aperture to receive the trocar. The membrane comprises an elongated wall portion which surrounds the aperture and an outer flange portion. Between the flange and the elongated wall is an intermediate, expandable, bellows-like portion which provides flexibility to a trocar inserted through the aperture. Adhesive material is disposed at the flange portion to enable the membrane to be adhered to a body surface. The aperture in the membrane which receives the trocar is sized with respect to the outer surface of the trocar disposed therein, so as to form a substantially tight fit and seal between the wall portion and the trocar.

5 Claims, 2 Drawing Sheets

TROCAR SUPPORT

CROSS REFERENCE TO RELATED APPLICATION

This application is a continuation-in-part of application Ser. No. 07/591,969, Filed Oct. 2, 1990 now abandoned.

BACKGROUND OF THE INVENTION

Recent advances in surgical procedures have involved the use of a trocar to minimize the size of incisions and the trauma of conventional surgery. A trocar, as known in the field, is a thin walled tubular member which is inserted through an incision in the skin into the area of a patient's body to be scanned or undergo a surgical procedure. The trocar is inserted into the body by means of a surgical knife or other instrument extendable through the trocar to create an incision with the trocar following the cutting implement through the incision. The surgeon places the trocar the desired depth into the body cavity and withdraws the cutting implement from within the tubular trocar and the appropriate surgical instrument is then inserted through the trocar. Thus, after implanting the trocar into the body cavity, it forms a housing for the insertion of various surgical instruments, including instruments for incision, evacuation, and endoscopy. Several trocars may be used in combination during a surgical procedure to avoid the need for a large and traumatic incision in the patient's body.

The outer end of the trocar is typically connected to a valving device, which permits the introduction of gas through the trocar into the body cavity to distend the cavity and facilitate the surgical procedure.

It is apparent that various problems may be encountered in the use of a trocar, such as described, to facilitate surgical procedures. For example, it is often desirable for the surgeon to have the trocar remain in proper position within the patient without the need to manually hold it in place. This frees the surgeon's hand so that the surgeon may direct attention to other trocars or other surgical needs. In addition, since it is common to distend the body cavity by the introduction of gas under pressure to provide the necessary space to perform the surgical procedure; it would be desirable to provide some gas sealing to prevent, or at least minimize, the escape of the gas around the incision through which the trocar is inserted. It is also important to provide sufficient flexibility in the trocar support to enable the trocar, and the surgical implements inserted therethrough, to be manipulated to a sufficient extent so that the required surgical procedure can be conducted and instruments can be changed without removing the trocar from the body.

The present invention, provides a trocar support which enables a trocar to be used for surgical procedures in an advantageous manner.

DESCRIPTION OF THE PRIOR ART

Many devices have been proposed to facilitate percutaneous incisions, most of which include passive supports, i.e., supports that just remain in place and cannot endure being manipulated without dislodging the instrument being supported. For example, Miller, U.S. Pat. No. 3,893,446, describes an abdominal catheter and means for securing the catheter in place in a patient. Another catheter-holding device is described by Petersen in U.S. Pat. No. 3,487,837. MacGregor, U.S. Pat. No. 4,579,120, describes a percutaneous lead and a technique for relieving the strain on the lead as well as for anchoring the lead where it exits from the body of a patient. Dalton, U.S. Pat. Nos. 4,464,178 and 4,632,671, also describe devices for anchoring a transcutaneous conduit. Hrushesky, U.S. Pat. No. 4,675,006, describes a support for a needle inserted into a body part of a patient which is in the form of a frusto-conical member, and Wallace, U.S. Pat. No. 2,898,917, discloses a surgical retaining device comprising a disc which can be adapted to conform and be anchored to a portion of the body of a patient, while Yamamoto, et al., U.S. Pat. No. 4,915,694, describes an antimicrobial catheter shield through which the catheter may be inserted.

Notwithstanding the foregoing, there remains a need for a support for a trocar which enables the trocar to be properly positioned within the body cavity after insertion thereof, as well as to provide a substantial seal around the trocar and the body surface, while permitting manipulation of the trocar within the body cavity.

SUMMARY OF THE INVENTION

The present invention is directed to a device which serves as a support for a trocar and provides a substantially tight seal around the trocar and against a body surface.

In accordance with the invention, there is provided a trocar support comprising an elastomeric membrane having an aperture to receive the trocar. The membrane comprises an elongated wall portion which surrounds the aperture and an outer flange portion. Between the flange and the elongated wall is an intermediate, expandable, portion configured like a bellows, herein referred to as a "bellows-like portion", which provides flexibility to a trocar inserted through the aperture. Adhesive material is disposed at the flange portion to enable the membrane to be adhered to a body surface. The aperture in the membrane which receives the trocar is sized with respect to the outer surface of the trocar disposed therein, so as to form a substantially tight fit and seal between the wall portion and the trocar. Preferably, the elongated wall portion is tapered toward the vertical centerline of the aperture to further facilitate insertion of the trocar into the support and to maintain a tight fit of the membrane around the trocar. Advantageously, a pressure-sensitive adhesive with a removable or peelable layer of protective material is provided on the flange of the membrane, so that when the trocar has been inserted into the patient's body, the membrane may be sealed to the body surface by removing the layer of protective material and applying pressure along the flange of the membrane against the body surface.

DESCRIPTION OF PREFERRED EMBODIMENTS

Figure 1:
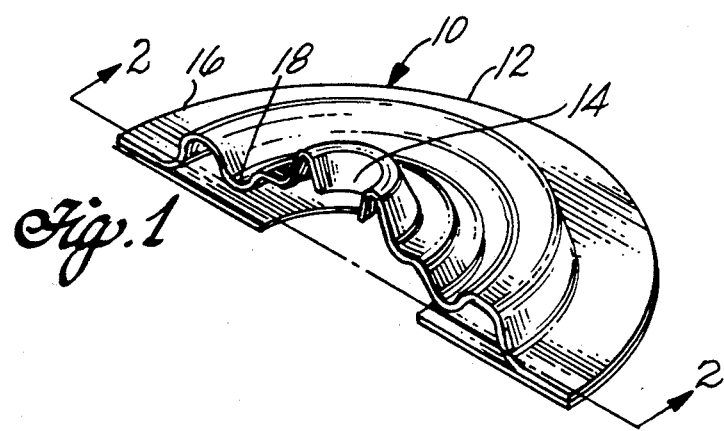
FIG. 1 is a perspective view, partially in section, of a trocar support in accordance with the invention.
Figure 2:
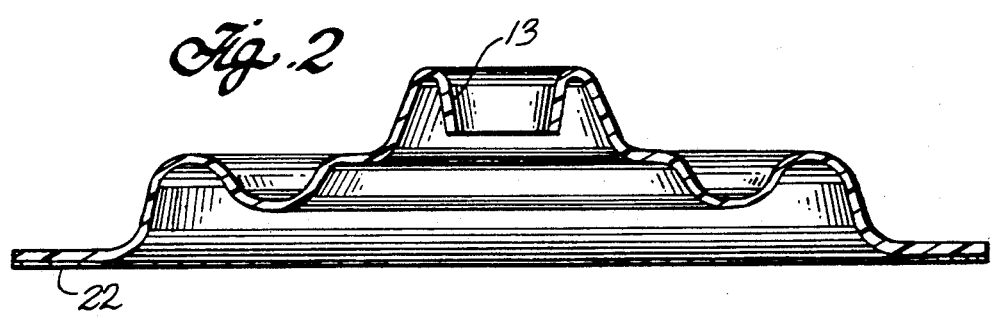
FIG. 2 is a side elevation view of the trocar support taken along 2—2 in FIG. 1.

Reference is made to the accompanying drawings, wherein like numerals refer to like parts. As can be seen, a trocar support 10 comprises a membrane 12 having an aperture 14 to accommodate the insertion therethrough of a trocar. At the outer perimeter of the membrane is a flange portion 16 and intermediate the flange portion and the aperture is an expandable bellows-like portion 18. An adhesive layer 22 is applied at the undersurface of flange 16. The adhesive layer may comprise a pressure-sensitive adhesive on a substrate which is bonded to the flange and which has a peelable protective cover layer or liner that may be removed just prior to adhering the trocar support to the body surface. The adhesive liner 22 may extend beyond the flange, if necessary, to provide sufficient adhesive surface to support the membrane in contact with the body surface even as the trocar is manipulated. A suitable adhesive is in the form of a laminate of a carrier, e.g., a plastic film, with adhesive applied, and a removable liner, e.g., paper, on the adhesive surface.

As can be seen, bellows-like portion 18 is able to flex before straining the adhesive bond to the body surface and the "memory" of the bellows material, i.e. its tendency to return to its normal position, provides strength to support the trocar.

The trocar can move through a conical angle of up to 70° to 80° from the vertical center line of the operation without imposing significant stress on the adhesive surface. Advantageously, the elongated walls 13 surrounding the aperture 14 are tapered toward the vertical center line of the aperture so that, upon insertion of the trocar through the aperture, the tapered wall is snugly fit around the outer surface of the trocar, thereby providing a substantial gas seal therebetween. Furthermore, because the wall makes a tight fit with the trocar, it can be used to support the trocar in place within the membrane and also to regulate the depth of penetration of the trocar into the body cavity. It has been found that a tapered inlet of at least 10° from the vertical, preferably 15° to 20° of the vertical, is sufficient for this purpose. Moreover, the aperture or orifice is desirably 20% to 25% smaller in diameter than the outside diameter of the trocar to provide a desired stretch-seal around the trocar. It may also be desirable to construct the trocar support with a greater thickness around the edge of the orifice; that is, at the elongated wall portion, to increase the strength of the support and the sealing for the trocar.

Figure 3:
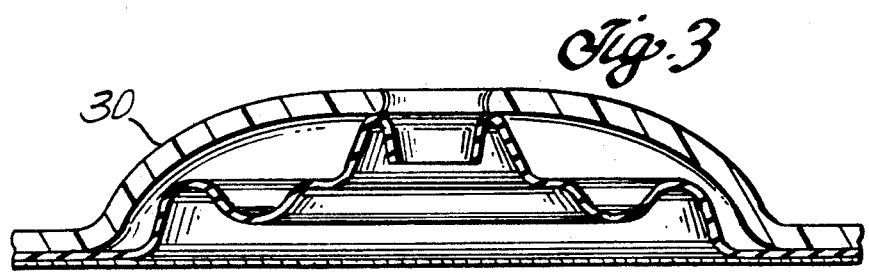
FIG. 3 is a side elevation view of another embodiment of the trocar support.

As can be seen in the embodiment illustrated in FIG. 3, a rigid support 30 may be provided over the expandable elastomeric membrane 18 to give additional support for the trocar without interfering with the flexibility afforded by the elastomeric membrane. In this embodiment, a rigid support member 30 is slidable on the body surface and is secured to the trocar around its periphery to help support the weight of the surgical implements which are supported by the trocar. Alternatively, the inner edge 32 of member 30 can be attached to the membrane 18 at the top of the elongated wall. Since the opposite end 34 is unconnected and free to move, the advantages of the flexible elastomeric membrane are retained.

Figure 4:
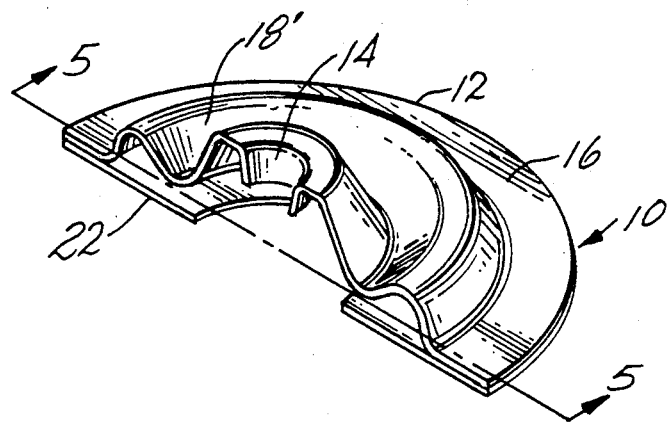
FIG. 4 is a perspective view, partially in section of another embodiment of the trocar support in accordance with the invention.
Figure 5:
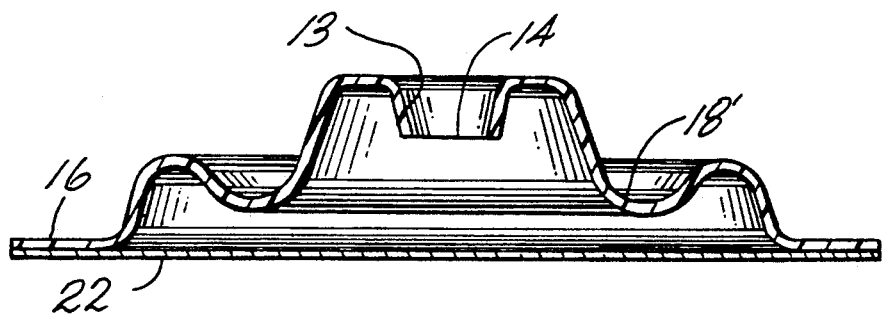
FIG. 5 is a side elevation view of the trocar support taken along lines 5—5 in FIG. 4.

The presently preferred embodiment is illustrated in FIGS. 4 and 5. Although the bellows configuration is varied from the design shown in FIG. 1, the overall construction of the trocar support 10 is the same; that is, the trocar support comprises a membrane 12 having a central aperture 14 to accommodate a trocar. At the outer perimeter of the membrane is a flange portion 16 and intermediate the flange portion and the aperture is an expandable bellows-like portion 18. As in the previously described embodiment, an adhesive layer 22 is applied at the undersurface of flange 16.

The membrane may be made by molding a thermoplastic elastomer to the desired configuration. Suitable elastomers are materials sold under the names "ALKRIN" and "VYTHENE" by Dupont and Alpha Chemical and Plastics Co., respectively. Clear elastomers such as "VYTHENE" are preferred. A wall thickness of 0.02 to 0.025 inches is sufficient to provide the desired degree of flexibility and expansion while preventing undesirable interference with the movability of the trocar. The bellows-like intermediate portion is provided with sufficient excess material to enable a trocar disposed in the membrane to circumscribe an arc of up to 70° to 80° from the vertical without imposing significant stress on the membrane.

A suitable pressure-sensitive, adhesive-containing liner is applied and bonded to the horizontal flange of the membrane to enable the membrane to be suitably adhered to the body surface and provide minimal lifting during any surgical procedures conducted through the trocar. An adhesive liner of about 0.003-inch is believed to be sufficient for this purpose since it allows for deformation of the skin surface during surgery, i.e., the peristolic action of the skin which tends to eject the trocar caused by the pushing and pulling of the surgical instruments through the trocar during the surgical procedure. A suitable pressure sensitive adhesive is "Avery MED 5502 FL Vinyl" available from the Specialty Tape Division of Avery Dennison.

During use, additional force to dislodge the trocar support results from the pressure of the gas introduced to the body cavity to distend the cavity to facilitate the surgical procedure. The presence of gas in the cavity causes further pressure on the skin, which is itself flexible, and could dislodge the trocar support if it is not adhered to the body surface satisfactorily.

As can be seen in the embodiment illustrated in FIG. 3, a rigid support 30 may be provided over the expandable elastomeric membrane 18 to give additional support for the trocar without interfering with the flexibility afforded by the elastomeric membrane. In this embodiment, a rigid support member 30 is slidable on the body surface and is secured to the trocar around its periphery to help support the weight of the surgical implements which are supported by the trocar. Alternatively, the inner edge 32 of member 30 can be attached to the membrane 18 at the top of the elongated wall. Since the opposite end 34 is unconnected and free to move, the advantages of the flexible elastomeric membrane are retained.

To use the trocar support of the present invention, the trocar is inserted through the aperture before it is positioned to make an incision in the body surface. The location of the support on the trocar is predetermined to enable the trocar to be inserted into the body cavity to the desired depth, after the trocar support is sealed in place on the body surface. The trocar is inserted through the skin by means of an obturator (knife) which penetrates the skin to enable insertion of the trocar into the body cavity, after which the obturator is removed. Either before or after the trocar is inserted and placed at the desired depth, the protective layer on the adhesive liner across the flange of the membrane is removed so that the membrane can be adhered to the body surface by the application of pressure. When used on the abdomen, a gas, such as carbon dioxide ($CO_2$), is introduced through the trocar to inflate the abdomen to provide a working environment for the surgery.

The trocar support thus stabilizes the trocar while the surgeon may be working with other implements inside the trocar and cannot take hold of the trocar itself to support it in position. The support also prevents the trocar from falling in or coming out of the incision, and makes controlling the instruments easier. The support additionally stabilizes the trocar in position so that it can be maintained at a predetermined penetration distance. Because the trocar support forms a substantial seal with the trocar and the body surface, the incision is sealed and the gas volume within the body cavity is stabilized, thus keeping the patient's organs from moving in relation to the surgical implements which have been inserted through the trocar. The surgeon is then better able to control the instruments relative to the organs for delicate surgery.

Because the support is made of flexible elastomeric material and is of a bellows-type construction, radical manipulation of the surgical instruments within the trocar is possible without disturbing the seal of the trocar support from the body surface by imposing excessive strain on the adhesive support. The membrane conforms to the skin movements during surgery and provides a seal around the incision.

It is apparent from the foregoing that the invention has important utility in connection with surgical procedures that utilize a trocar, such as in laparoscopic procedures. The trocar supports may be provided in different sizes and with apertures of different size to accommodate trocars of different sizes. Changes and modifications may be made without departing from the spirit of the invention and, accordingly, the scope of the invention should be limited only by the appended claims wherein:

What is claimed is:

1. A trocar support comprising:
   an elastomeric membrane having an aperture therein for receiving a trocar having an outer surface;
   said membrane comprising three portions, an elongated wall potion surrounding said aperture, an outer flange portion, and an expandable bellowed intermediate portion therebetween; and
   adhesive material at the flange portion to enable said membrane to adhere to a body surface;
   said aperture being sized with respect to the outer surface of a trocar to be disposed therein so as to form a tight fit and seal between the wall portion and the trocar, said intermediate portion being expandable to enable a trocar therein to circumscribe an arc from a vertical centerline without imposing undue stress upon the adhesive surface of the flange portion.

2. A trocar support according to claim 1 wherein said adhesive is a pressure-sensitive adhesive.

3. A trocar support according to claim 2 further comprising a removable layer of protective material applied to said adhesive that can be removed prior to applying pressure to adhere said membrane to a body surface.

4. A trocar support according to claim 1 wherein said arc is up to 70 to 80 from the vertical centerline without imposing undue stress which would dislodge the trocar support.

5. A trocar support according to claim 1 wherein the elongated wall portion is tapered toward the vertical centerline of the aperture to facilitate insertion of the trocar and to provide a tight fit and seal with the outer surface of a trocar to be disposed therein.

* * * * *

UNITED STATES PATENT AND TRADEMARK OFFICE
CERTIFICATE OF CORRECTION

PATENT NO. : 5,073,169
DATED : December 17, 1991
INVENTOR(S) : Steve Raiken; Bruce B. McLucas It is certified that error appears in the above-identified patent and that said Letters Patent is hereby corrected as shown below:

On the Title Page:

[76] Inventor: change "Steve Raiken, 5152 Pickford Way, Culver City, Calif. 90230"

to

[76] Inventors:  -- Steve Raiken, Culver City; Bruce B. McLucas, Pacific Palisades, both of Calif. --

Signed and Sealed this

Twenty-seventh Day of December, 1994

Attest:

BRUCE LEHMAN

Attesting Officer          Commissioner of Patents and Trademarks